United States Patent [19]

Pinnell

[11] Patent Number: 4,645,668

[45] Date of Patent: Feb. 24, 1987

[54] METHOD FOR THE PREVENTION AND TREATMENT OF SCARS WITH ENZYMES

[75] Inventor: Sheldon R. Pinnell, Durham, N.C.

[73] Assignee: Biospecifics, NV, Curacao, Netherlands Antilles

[21] Appl. No.: 716,742

[22] Filed: Mar. 27, 1985

Related U.S. Application Data

[63] Continuation-in-part of Ser. No. 520,203, Aug. 4, 1983, Pat. No. 4,524,065.

[51] Int. Cl.$^4$ ............................................. A61K 37/48
[52] U.S. Cl. ...................................................... 424/94
[58] Field of Search .......................................... 424/94

[56] References Cited

U.S. PATENT DOCUMENTS

| | | | |
|---|---|---|---|
| 3,003,917 | 10/1961 | Beiler et al. | 424/94 |
| 3,019,167 | 1/1962 | Innerfield | 424/94 |
| 3,019,171 | 1/1962 | Bloch et al. | 424/94 |
| 4,197,291 | 4/1980 | Klein et al. | 424/94 |
| 4,276,281 | 6/1981 | Crikelair | 424/94 |
| 4,524,065 | 6/1985 | Pinnell | 424/94 |

OTHER PUBLICATIONS

Kuhn III, C. et al., The Induction of Emphysema with Elastase, II. Changes in Connective Tissue, Lab. Invest. 34: 372–380, 1976.

Janoff, A. et al., Experimental Emphysema Induced with Purified Human Neutrophil Elastase: Tissue Localization of the Instilled Protease, Am. Review of Respiratory Disease 115: 461–478, 1977.

Senior, R. M. et al., The Induction of Pulmonary Emphysema with Human Leukocyte Elastase, American Review of Respiratory Disease, 116: 469–475, 1977.

Gross, P. et al., Experimental Emphysema: Its Production with Papain in Normal and Silicotic Rats, Arch. Environ. Health, 11: 50–58, 1965.

Hayes, J. A. et al., The Pathology of Elastase-Induced Panacinar Emphysema in Hamsters, The Journal of Pathology, 117 No. 1: 1–14, 1975.

Goldring, I. P. et al., On the Production of Emphysema in Syrian Hamsters by Aerosol Inhalation of Papain, Arch. Environ. Health, 16: 59–60, 1968.

Liotta, L. A. et al., Identification of a Type V Collagenolytic Enzyme, Biochemical and Biophysical Research Communications, 98: 184–190, 1981.

Liotta, L. A. et al., Partial Purification and Characterization of a Neutral Protease Which Cleaves Type IV Collagen, Biochemistry, 20: 100–104, 1981.

Werb, Z. et al., Degradation of Connective Tissue Matrices by Macrophages. I. Proteolysis of Elastin, Glycoproteins, and Collagen by Proteinases Isolated from Macrophages, Journal of Experimental Medicine, 152: 1340–1357, 1980.

Moscatelli, D. et al., in *Proteinases and Tumor Invasion*, Raven Press, pp. 143–152, 1980.

*Primary Examiner*—Sam Rosen
*Attorney, Agent, or Firm*—Roland Plottel

[57] ABSTRACT

The method for preventing and for treating mammalian cicatrices such as keloids, acne scars, hypertrophic scars, wrinkles, cellulite and neoplastic fibrosis which comprises intra-dermal injection of effective amounts of a pharmacologically suitable solution of the enzymes collagenase, elastase, papain, plasminogen activator, plasmin, mast cell protease or lysosomal hydrolase, individually, and one or more of such enzymes in combination with the enzyme hyaluronidase.

10 Claims, No Drawings

METHOD FOR THE PREVENTION AND TREATMENT OF SCARS WITH ENZYMES

CROSS REFERENCE TO RELATED APPLICATION

This application is a continuation-in-part of copending application Ser. No. 520,203 filed Aug. 4, 1983, which issued June 18, 1985 as U.S. Pat. No. 4,524,065.

BACKGROUND OF THE INVENTION

Collagen is the major structural constituent of mammalian organisms and makes up a large portion of the total protein content of skin and other parts of the animal body. In humans, it is particularly important in the wound healing process and in the process of natural aging. Various skin traumas such as burns, surgery, infection and accident are often characterized by the erratic accumulation of fibrous tissue rich in collagen and having increased proteoglycan content. In addition to the replacement of the normal tissue which has been damaged or destroyed, excessive and disfiguring deposits of new tissue sometimes form during the healing process. The excess collagen deposition has been attributed to a disturbance in the balance between collagen synthesis and collagen degradation.

Keloids are tumors or connective tissue consisting of highly hyperplastic masses which occur in the dermis and adjacent subcutaneous tissue in certain susceptible individuals, most commonly following trauma. The known therapies for keloids have had limited success and they frequently can recur in the site after surgical removal.

Hypertrophic scars are unsightly masses which can result from burns or other injuries to the skin. Such scars are usually permanent and resistant to known methods of therapy.

Depressed scars occur following inflammatory conditions and result in contraction of the skin, leaving a cosmetically unacceptable result. The most common example is the scarring which occurs following inflammatory acne. The condition is common and permanent. The depression occurs as a normal consequence of healing and the scar tissue causing the depression is predominantly composed of collagen.

Post-surgical adhesions sometimes form following surgery or inflammation, wherein the normal healing process may bind structures one to another. An undesirable example is the binding of tendons to tendon sheath. Such adhesions are common complications of surgery and no therapy is available. Collagen is a predominant part of this scarring process.

Acne vulgaris is another common skin disease often causing unsightly facial scars. Some acne patients have been successfully treated for acne scarring using intralesional steroids, liquid nitrogen, dermabrasion and the like. In many cases, however, the lesions do not respond or the treatment results in other complications.

Additional disfiguring conditions such as wrinkling, cellulite formation and neoplastic fibrosis also appear to result from excessive collagen deposition which produces unwanted binding and distortion of normal tissue architecture.

Enzymes are proteinaceous substances which act as catalysts for biological reactions; in some cases hydrolysis reactions and in others oxidation-reduction processes. Some enzymes have broad activity and others, such as collagenase (Clostridiopeptidase A) produced from the bacterium *Clostridium hystolyticum*, have very specific activity. Highly purified collagenase has been prepared and been found uniquely capable of cleaving bonds in the collagen structure permitting other enzymes to act on the resulting molecular fragments.

The use of collagenase in medical practice is well known but has heretofore been limited to topical application for debridement of dermal ulcers and burns and, recently, for the treatment of prolapsed intervertebral discs. Purified collagenase has been demonstrated to be relatively safe even in large doses (thousands of units) in animals and in contact with human blood vessels, nerves and bones.

Hyaluronidase is a soluble enzyme product prepared from mammalian testes. It has been previously used in human medicine to increase the effect of local anesthetics and to permit wider infiltration of subcutaneously administered fluids.

Elastase is an enzyme obtained from dried pancreas or from leukocytic origins and which can be electrophoretically or otherwise purified and standardized by assay. The most characteristic trait of elastases is its capacity to break down elastin, the specific protein of elastic fibers.

Papain is a proteolytic enzyme or mixture of enzymes prepared from papaya fruit which hydrolyzes polypeptides, amides and esters, yielding peptides of lower molecular weight. It is one of the most thermostable enzymes and has commercial uses in the food industry.

Plasminogen activator is a neutral proteinase secreted by mononuclear phagocytes, prominent cells in the host defense characteristic of chronic inflammatory responses. Plasminogen activator is believed to mediate extracellular protein degradation by macrophages in the presence of plasmonogen.

Plasmin is a proteolytic enzyme, derived from the activation of human plasminogen by highly purified streptokinase, which dissolves fibrin. Plasmin has fibrinolytic properties and also contains a plasminogen activator. It has been used for the treatment of thrombotic disorders, as an adjunct to anti-coagulant therapy and for the debridement of wounds in conjunction with deoxyribonuclease.

Lysosomal hydrolase is an enzyme derived from body cells, e.g. the liver, which catalyzes the removal of water from a substrate. It has been hypothesized that the degradation of connective tissue involves two distinct steps—an initial extracellular cleavage of insoluble proteins mediated by neutral proteinases, followed by endocytosis and completion of digestion within lysosomes.

Mast cell protease is a neutral proteolytic enzyme extracted from the media or cultured metastatic tumor cells and highly purified by sequential ammonium sulfate fractionization, column chromatography and molecular sieve chromatography. It has been shown to be especially effective in cleaving type IV collagen.

SUMMARY OF THE INVENTION

The present invention comprehends the method of treating conditions in humans and animals associated with excessive fibrosis to restore normal appearance as well as the remodeling of unwanted fibrous tissue to obtain more acceptable cosmetic appearance by injecting directly into the disfiguring lesions an effective amount of the enzymes collagenase elastase, papain, plasminogen activator, plasmin, mast cell protease or lysosomal hydrolase, individually, and one or more of such enzymes in combination with the enzyme hyaluronidase.

The present invention also includes the method of preventing the formation of disfiguring scars during the healing process following trauma which comprises administration of an effective amount of collagenase, individually, and one or more of such enzymes in combination with hyaluronidase.

More particularly, it is the object of this invention to provide new, non-surgical and non-radical procedures for preventing and for treating objectionable cicatrices in animals and humans. It is believed that the use of enzymes in the prevention and treatment of disfiguring scars represents a significant advance in the art.

These and other objects and advantages of this invention will be apparent from the more detailed description which follows.

DESCRIPTION OF THE PREFERRED EMBODIMENTS

Purified collagenase, free of detectable caseinase and non-specific protease activity is manufactured by Advance Biofactures Corporation, Lynbrook, New York. The frozen enzyme is thawed and diluted with normal saline solution plus 2 mM calcium chloride to the desired concentration. Enzyme activity, given in ABC units, is determined using an insoluble substrate, undenatured bovine tendon, according to a modification of the method of Mandl et al (Arch Biochem Biophys 74:465–475, 1958). A unit of activity corresponds to the release of ninhydrin reactive material equivalent to nanomoles leucine equivalents released in one minute from undenatured collagen. Collagenase is obtained from culture of a special strain of *Clostridium histolyticum* and purified by a chromatographic technique.

Hyaluronidase (Wydase) is manufactured by Wyeth Laboratories, Philadelphia, Pa. It is a preparation of highly purified bovine testicular hyaluronidase and is available dehydrated in the frozen state under high vacuum. The N.F. Hyaluronidase Unit is equivalent to the turbidity-reducing (TR) unit and the International Unit.

The following Examples are presented for the purpose of illustrating the invention:

EXAMPLE I

A male patient with an abdominal keloid resulting from an old surgical procedure is medically screened and found qualified for enzyme therapy. The patient receives four injections, 0.1 ml. each, containing 50, 100, 250 and 500 units of collagenase respectively, directly into the lesion. The patient is observed for one hour after the injections for allergic reactions or other effects. The patient returns after one month for laboratory work and assessment of the concentration giving him the best therapeutic response. He thereafter receives additional injections of the optimum concentration at appropriate intervals until the desired keloid size reduction is achieved.

EXAMPLE II

A male patient with a disfiguring hypertrophic scar, resulting from an earlier trauma, is medically screened and found suitable for enzyme therapy. The scar is multiply injected with 250 units of collagenase combined with 150 units of hyaluronidase in a total volume of 0.2 ml. per injection. Further intralegional injections of the same components and concentrations are given at monthly intervals. Therapy is terminated when the desired reduction in scar size is achieved or failure of improvement between treatments is noted.

EXAMPLE III

A female patient with a prior history of disfiguring surgical scar formation is examined during convalescence from surgery and found to be producing keloidal tissue in the new incision. She is medically screened and found otherwise suitable for enzyme therapy. Multiple intralesional injections of 50 units of collagenase combined with 150 units of hyaluronidase in a total volume of 0.2 ml. per injection are made at one week intervals. Therapy is discontinued when scar healing is completed or when no further improvement in scar architecture is noted.

EXAMPLE IV

A female patient with multiple acne scars of both closed comedo-like character and "ice-pick" type is medically screened and found suitable for enzyme therapy. The scars are injected with 100 units of collagenase in a total volume of 0.1 ml. per injection. The patient returns after one month for laboratory tests and evaluation of the clinical response. The total number of treatment visits is six or fewer to achieve substantial improvement in overall skin contour.

EXAMPLE V

A female patient with depressions on her thighs caused by fibrotic bands in the fatty connective tissue, commonly called cellulite, is medically screened and found suitable for enzyme therapy. Multiple injections of 100 units of collagenase combined with 150 units of hyaluronidase in a total volume of 0.2 ml. per injecton are made in the affected area. Therapy continues at intervals of two weeks until the desired improvement in skin contour is achieved.

In view of the preceding description, further modifications and alternative embodiments of the instant invention will be apparent to those skilled in the art. Accordingly, the preceding descriptions and examples are to be construed as explanatory and illustrative only and are for the purpose of teaching and enabling those skilled in the art to practice this invention. It should be understood that the amount of the pharmacologically suitable solution of enzymes required for the dissolution of mammalian cicatrices will vary. Suitable amounts can be determined from a reasonable number of experiments and the following factors should be considered: the nature of the cicatrix being treated, the concentration of enzymes in the solution, the type of enzymes used, the amount, location and nature of the fibers to be dissolved as well as the nature of the tissue adjacent to the cicatrix being treated.

While the preferred embodiment of the above described invention is to be understood to be the best mode presently contemplated, it is by no means the only embodiment possible. The scope of the invention is defined by the following claims and by any equivalent modifications and variations that fall within the true spirit of the invention.

What is claimed is:

1. A method for the dissolution of mammalian cicatrices which comprises administering an effective amount of an enzyme selected from the group consisting of elastase, papain, plasminogen activator, plasmin, mast cell protease and lysosomol hydrolase directly into the lesion.

2. The method of claim 1 wherein the elastase is electrophoretically purified porcine pancreatic elastase.

3. The method of claim 1 wherein the elastase is human neutrophilic polymorphonuclear leukocyte elastase purified by affinity chromatography.

4. The method of claim 1 wherein the elastases is purified from the conditioned medium of thioglycollate-elicited mouse macrophages.

5. The method of claim 1 wherein the plasmin is bovine or human plasmin prepared by activating plasminogen with urokinase.

6. The method of claim 1 wherein the mast cell protease is the highly purified neutral extract from the media of cultured metastatic tumor cells.

7. A method for the dissolution of mammalian cicatrices which comprises administering an effective amount of an enzyme selected from the group consisting of elastase, papain, plasminogen activator, plasmin, mast cell protease and lysosomal hydrolase in combination with an effective amount of the enzyme collagenase directly into the lesion.

8. A method for the dissolution of mammalian cicatrices which comprises administering an effective amount of an enzyme selected from the group consisting of elastase, papain, plasminogen activator, plasmin, mast cell protease and lysosomal hydrolase in combination with an effective amount of the enzyme hyaluronidase directly into the lesion.

9. A method for the prevention of mammalian cicatrices which comprises administering an effective amount of an enzyme selected from the group consisting of elastase, papain, plasminogen activator, plasmin, mast cell protease and lysosomal hydrolase in combination with an effective amount of the enzyme collagenase directly into the affected area during the healing process.

10. A method for the prevention of mammalian cicatrices which comprises administering an effective amount of an enzyme selected from the group consisting of elastase, papain, plasminogen activator, plasmin, mast cell protease and lysosomal hydrolase in combination with an effective amount of the enzyme hyaluronidase directly into the affected area during the healing process.

* * * * *